United States Patent [19]

Petralli

[11] Patent Number: 5,084,629
[45] Date of Patent: * Jan. 28, 1992

[54] SPLIT FLOW UNIFORM MULTISENSOR DETECTION

[75] Inventor: Louis J. Petralli, Grants Pass, Oreg.

[73] Assignee: Met One, Inc., Grants Pass, Oreg.

[*] Notice: The portion of the term of this patent subsequent to Jul. 30, 2008 has been disclaimed.

[21] Appl. No.: 520,110

[22] Filed: May 7, 1990

[51] Int. Cl.$^5$ .............................................. G01N 15/06
[52] U.S. Cl. ..................................... 250/573; 250/576; 356/343
[58] Field of Search ............... 250/573, 574, 575, 576; 356/342, 343

[56] References Cited

U.S. PATENT DOCUMENTS

| | | | |
|---|---|---|---|
| 2,675,697 | 4/1954 | Quynn et al. | |
| 3,915,570 | 10/1975 | Skala | 250/573 |
| 4,639,137 | 1/1987 | Hazan et al. | 356/343 |
| 4,798,465 | 1/1989 | Knollenberg | 356/336 |
| 4,816,695 | 3/1989 | Lavin | 250/573 |
| 4,907,884 | 3/1990 | Wyatt et al. | 356/343 |
| 4,920,275 | 4/1990 | Itoh | 250/574 |
| 4,989,974 | 2/1991 | Anton et al. | 250/576 |

OTHER PUBLICATIONS

"CNC Sensor for Clean Room Monitoring", 1986 Proceedings—Institute of Environmental Sciences, pp. 439-444—Fukushima, N. et al.

"A Case for Continuous Multipoint Particle Monitoring in Semiconductor Clean Rooms", 1986 Proceedings—Institute of Environmental Sciences, pp. 432-438—Sem, Gilmore J.

Primary Examiner—David C. Nelms
Assistant Examiner—Que T. Le
Attorney, Agent, or Firm—Schneck & McHugh

[57] ABSTRACT

An apparatus for detecting and counting particles in a gas stream flowing at a preselected rate, wherein the apparatus includes a multi-tier inlet manifold and a plurality of sensors. The inlet manifold divides an aggregate sample flow into a plurality of substantially identical partial sample flows. Each partial sample flow enters one of the functionally duplicative sensors and is intersected by an incident beam to define a view volume. Particles contained within the partial sample flows scatter light as the particles pass through the view volume. The scattered light is directed to a photodetector which provides a signal having characteristics corresponding to the sensed light. Particle detection in each view volume is operationally independent of the others, but the information is combined to provide a total particle count of the aggregate sample flow.

20 Claims, 3 Drawing Sheets

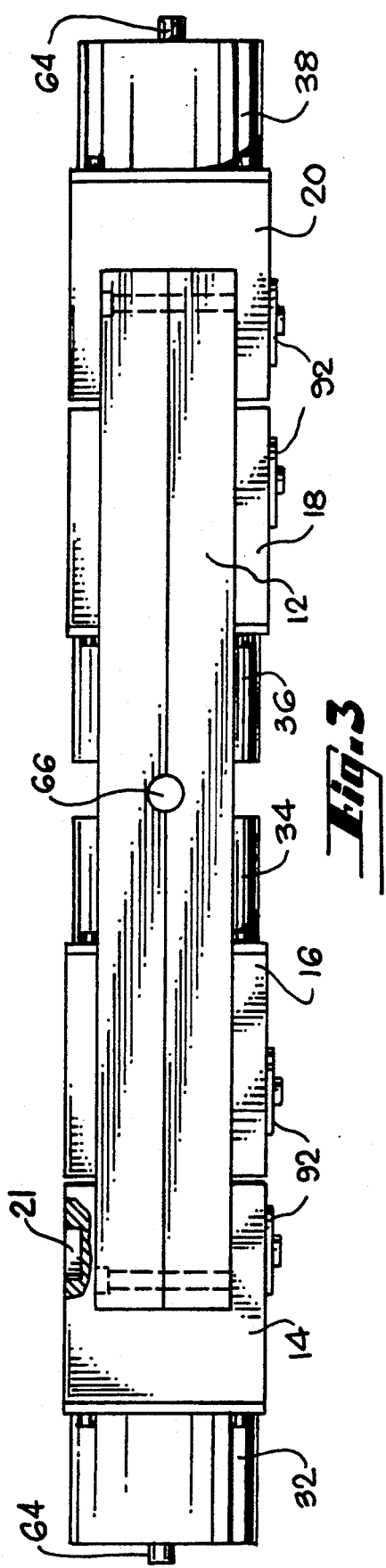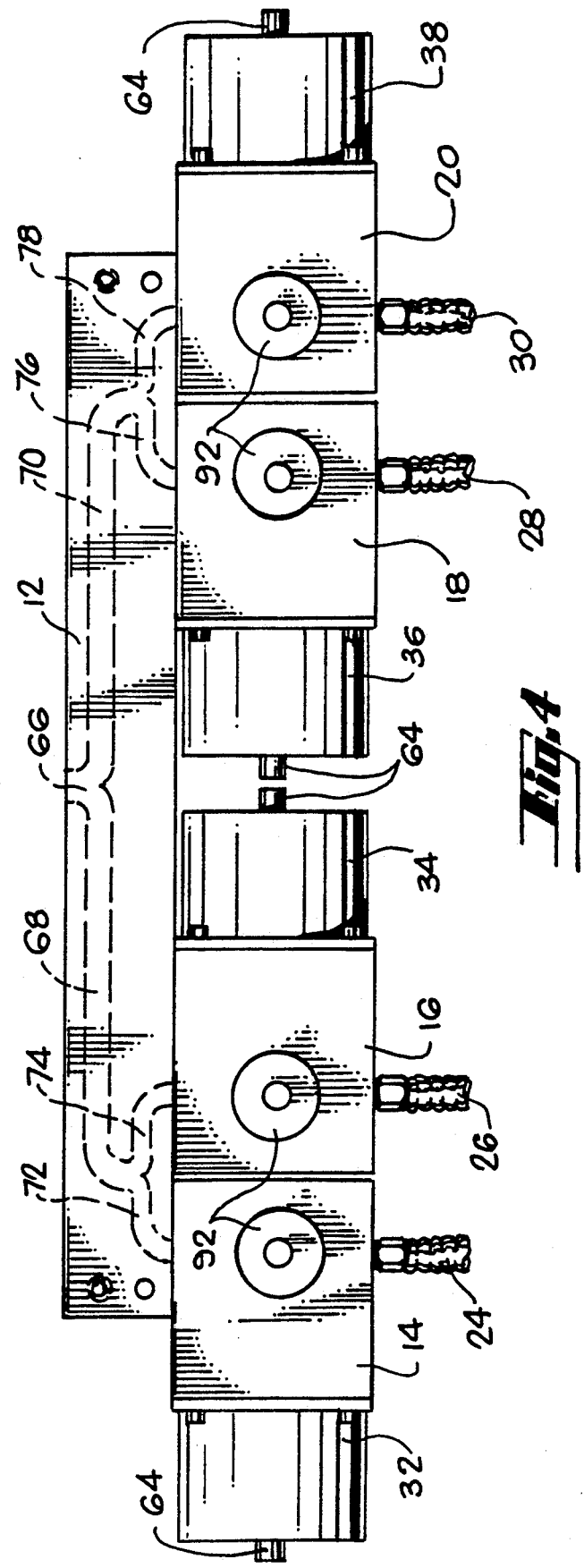

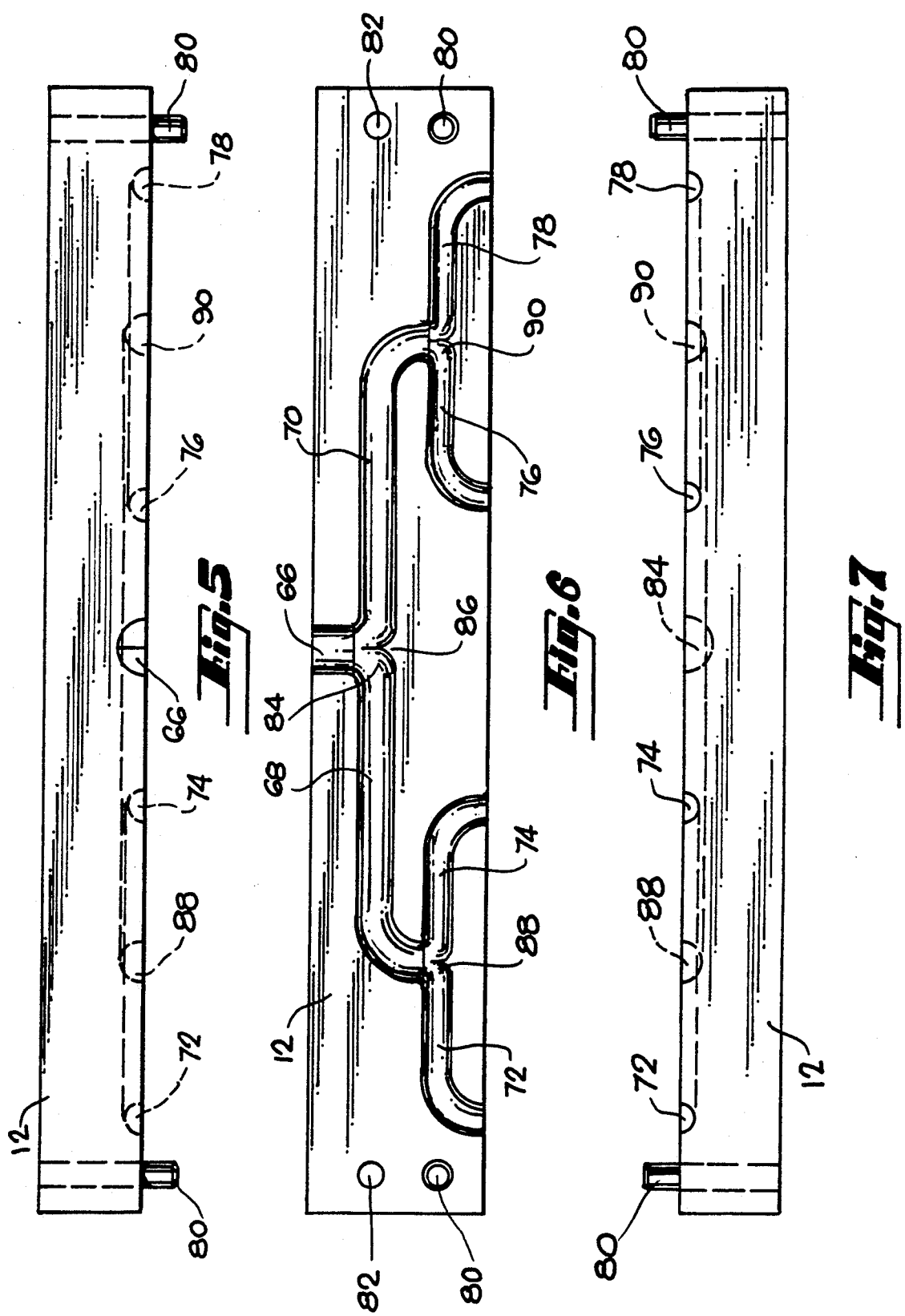

SPLIT FLOW UNIFORM MULTISENSOR DETECTION

TECHNICAL FIELD

The present invention relates generally to particle size measurement apparatus and particularly to apparatus for determining the size and concentration of particles in a fluid.

BACKGROUND ART

Devices which measure and count particles in a fluid are well known. Such devices are employed, for example, by semiconductor wafer manufacturers to monitor the extent of airborne particulate matter in a clean room. Pharmaceutical manufacturers employ such devices for the detection and control of foreign particles.

One method of particle detection is light blockage particle counting, or light obscuration. Light obscuration sensors work on the principle of the casting of a shadow onto a photodetector as a flow of particle-laden fluid is directed through a light beam generated by an incandescent lamp. A more sensitive method is the light scattering method. As a particle passes through a light beam, the particle scatters light. For a stationary particle the amount of scattered light is a function of the particle size, the wavelength and intensity of the incident light, and the difference between the light scattering properties of the particle and the surrounding medium. A laser source may be used to generate the light beam and the scattered light is sensed by a detector which provides readable signals indicative of particle size.

In employment of the light scattering method other factors must be considered in the detection of particles which are in motion, rather than, stationary. In particle-detection applications such as clean room monitoring, the flow rate of a given volume is typically a standard rate, for example, one cubic foot per minute. U.S. Pat. No. 4,798,465 to Knollenberg teaches the benefits of a sample flow rate of one cfm. However, the velocity of a sample flow determines the time in which a particle remains within the view volume of a detection device. The quantity of light which a given-sized particle will scatter while in the view volume is inversely proportional to particle velocity and directly proportional to particle size. Increasing the velocity of a particle by a factor of two results in a halving of the time span in which the particle travels through the view volume, thereby decreasing the quantity of light scattered by the particle.

Typically there is a direct relation between counter sample rate, counter size, and counter cost. For example, Knollenberg teaches a detection device having a sensing region for detecting and counting particles which scatter the light from a laser beam. A linear array of detectors is used, with each detector monitoring a different portion of the single sensing region. The patent teaches that use of a linear array of detectors enables sensing of particles of 0.1 micron even in the high background of molecular scattering associated with a flow rate of 1 cfm.

An object of the present invention is to provide an apparatus for detecting and counting particles with a relatively high sensitivity but in a cost-efficient and compact manner.

SUMMARY OF THE INVENTION

The above object has been met by a particle counting apparatus with apportionment of a supply of gas flow at a preselected set rate into a plurality of partial gas flows with particle-counting detection by a corresponding number of functionally duplicative sensors.

The apparatus includes a manifold having an inlet and a plurality of outlets, with a dividing structure of passageways from the upstream inlet to the downstream outlets. Each division of passageways is a division of a single upstream passageway to a pair of downstream passageways so that the dividing structure of the manifold defines a plurality of tiers. The passageways increase by a factor of two from an upstream tier to a downstream tier but the sum of the cross sectional areas of the passageways are equal. Moreover, all passageways are defined by smooth radius turns.

The individual sensors each have a flow path therethrough in fluid communication with an outlet of the manifold. Each sensor has a light source, typically a laser diode, for projecting an incident beam in a direction to intersect the flow path and further has a detector for sensing light scattered as the incident beam strikes particles suspended in a gas flow through the flow path of the sensor. Each sensor monitors a portion of the preselected set flow rate at the inlet of the manifold. For example, a flow rate of 1 cfm at the manifold inlet may be divided into ten partial streams of 0.1 cfm each.

An advantage of the present invention is that particle counting can occur at a relatively high flow rate while maintaining the particle-sizing sensitivity of an individual sensor. The velocity of a sample flow affects sensitivity in two ways. Firstly, as noted above, the quantity of light which a given-sized particle will scatter while in a view volume is inversely proportional to particle velocity. Decreasing the velocity of a particle by a factor of two doubles the time span in which the particle travels to the view volume, thereby increasing the quantity of light scattered by the particle.

Secondly, detection of a particle results in generation of a pulse having characteristics corresponding to that detection. The time in which the particle remains in the view volume determines the pulse width. Pulse width plays an important part in optimizing the signal-to-noise ratio of a particle counter. Particle velocity fixes the minimum time in which a particle travels through the view volume of the incident beam, which in turn governs the minimum pulse width which is produced by the detector electronics. Fast pulses require an increase in the electronic high frequency response corner. Raising the high frequency response corner increases the amount of amplifier noise, thus degrading the signal-to-noise ratio of the particle counter. The present invention, however, permits real time particle counting of 1 cfm, without requiring the expensive sensors normally necessary for high sensitivity at the 1 cfm flow rate.

BRIEF DESCRIPTION OF THE DRAWINGS

FIG. 3 is a top view of the apparatus of FIG. 1.

FIG. 4 is a side view of the apparatus of FIG. 3.

FIG. 5 is a top view of a portion of the manifold of FIG. 4.

FIG. 6 is a side view of the manifold of FIG. 5.
FIG. 7 is a bottom view of the manifold of FIG. 6.

BEST MODE FOR CARRYING OUT THE INVENTION

Figure 1:
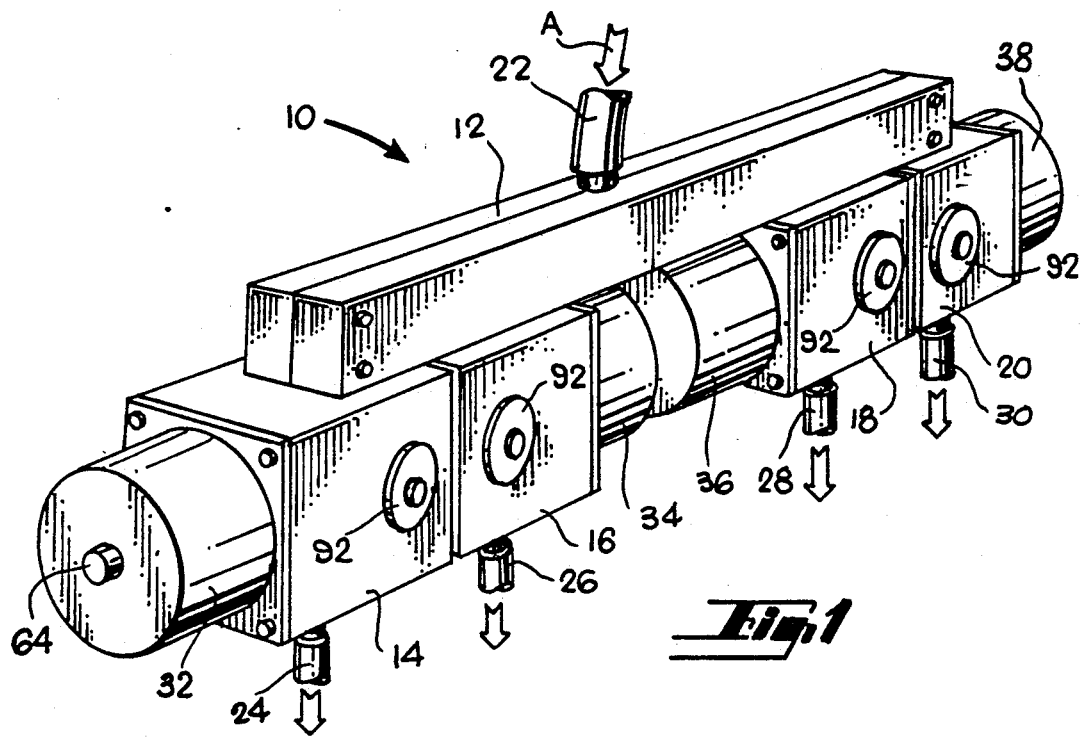
FIG. 1 is a perspective v o a multisensor particle counting apparatus in accord with the present invention.

With reference to FIG. 1, the multisensor particle counter 10 includes a manifold 12 and four sensors 14, 16, 18 and 20. The sensors 14–20 are shown as connected only by attachment to the manifold 12, but this is not critical. Typically, the four sensors are connected to a chassis and are housed along with the manifold within a containment structure. Moreover, the sensors may be part of a single body, rather than stand alone devices.

The sensors 14–20 as illustrated are stand alone devices. Preferably the sensors are laser diode sensors. Such sensors may have dimensions of two inches high, two inches wide, and four inches long. Cost efficient, low voltage laser diodes for use with the sensors are known and used in the art. The positioning of a laser diode 21 is shown in a cutaway portion of FIG. 3. A typical sensitivity may be an ability to detect particles of 0.3 micron at a flow rate of 0.1 cfm. Particle sensitivity is inversely proportional to flow rate through the sensor. Returning conduit 22 at the inlet of the manifold 12 is in fluid communication with a supply of particle-laden gas having a preselected flow rate. The inlet stream is exactingly segmented to provide four identical partial flows which exit from the sensors at hoses 24, 26, 28 and 30.

Figure 2:
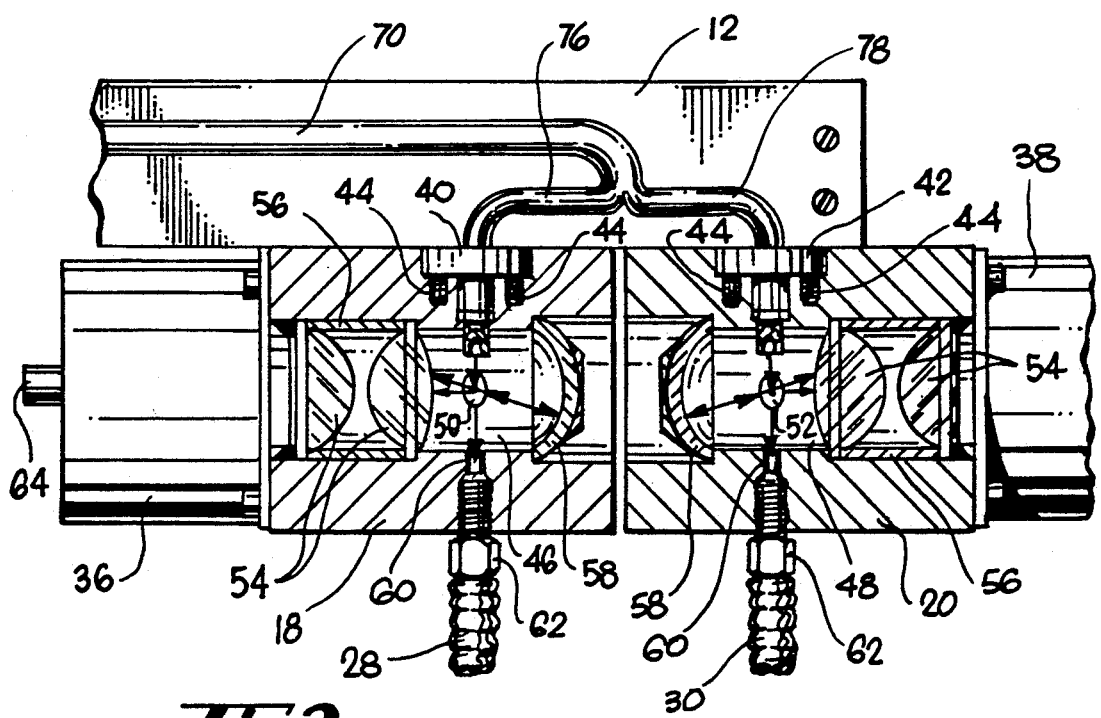
FIG. 2 is a partial side sectional view of a pair of sensors of FIG. 1.

Referring now to FIGS. 1 and 2, each sensor 14–20 includes a detector 32, 34, 36 and 38 for monitoring fluid flow. The aggregate sample flow, indicated by arrow A, is drawn into the inlet manifold 12 from the aerosol inlet conduit 22. Particle-bearing gas, typically air, enters the manifold and is split once and then split again to provide four separate flows, preferably of equal flow rates. The four separate partial sample flows are received at the sensors 14–20. As best shown in FIG. 2, each sensor 18 and 20 has a nozzle 40 and 42 secured to the sensor body by threaded fasteners 44.

The nozzle 40 and 42 of a sensor 18 and 20 acts as an inlet port for the particle-bearing gas into a sensor cavity 46 and 48. The partial sample flow through the cavity intersects the incident beam, represented by ellipse 50 and 52, of the associated laser diode. The view volume of the sensors is defined by the intersection of the incident beam with the sample flow which enters from the nozzles 40 and 42 and is exhausted through the hose 28 and 30.

A particle contained within a partial sample flow through the view volume of a sensor 18 and 20 causes a scattering of light as the particle is impinged by the incident beam 50 and 52 of the laser diode. Light is scattered in many directions. A portion of the scattered light is directed at a lens system 54 which is secured in position by a cylindrical member 56. A second portion of the scattered light is reflected by a concave spherical reflector 58 which reflects the energy back through the view volume to the lens system 54. The lens system focuses the radiation to a photodetector, such as a photodiode, within the associated detector 36 and 38. The photodetector, not shown, provides an electrical signal which has a characteristic corresponding to the energy received from the lens system. The partial sample flow exits the sensor cavity through an exhaust port 60 that leads to an externally threaded fitting 62 which is press fit to the outlet hose 28 and 30. The electrical signal provided by the detector 36 is conducted through a wire, not shown, attached to a connector 64 on the detector. High speed signal processing and data management then convert the scattered light measurement into particle size and number readings. Measurements of scattered light are combined in a manner to provide a particle count for the aggregate sample flow which enters through the aerosol inlet conduit 22 shown in FIG. 1.

Referring now to FIGS. 3 and 4, the structure of the passageways for particle-bearing gas through the inlet manifold 12 is an important feature in obtaining an accurate reading of a particle count in a clean room or the like. Large particles which strike the walls of a passageway can be broken into smaller particles, thereby creating an inaccurate particle count and indication of particle size. Moreover, where a flow is divided into individual partial flows, unless downstream passageways have the same cross sectional area as the original, there will be changes in temperature, pressure and velocity. A change in pressure may cause evaporation or condensation of vapors, thereby jeopardizing the particle count. A decrease in velocity may result in settling out of large particles. Moreover, turns within flow passageways may cause collisions between a particle and the wall of a passageway, causing a breakup of the particle and rendering inaccurate any quantitative and qualitative analysis of the atmosphere of a clean room.

The inlet manifold 12 shown in FIGS. 3 and 4 includes an inlet 66 which is divided into a pair of reduced passageways 68 and 70. Each of the reduced passageways is bisected to provide four outlet passageways 72, 74, 76 and 78. The outlet passageways supply each of the sensors 14–20 with a partial gas flow for detection of particles suspended within the flow.

The construction of the manifold 12 is best seen in FIGS. 5–7. The manifold is made of a pair of blocks having matching grooves which are joined to form the passageways 66–78 by insertion of rods 80 on one block into bores 82 of the other block. Only one block is shown in FIGS. 5–7.

At a division 84 of the inlet 66, the bisection of the gas stream is defined by smooth radius turns and a center indent 86. The construction reduces the risk of particle breakup as particles make contact with the walls of the reduced passageways 68 and 70. A collision of a particle against a wall may divide the particle, whereafter the particle will be read as a pair of smaller particles. This jeopardizes the quantitative and qualitative analysis of the atmosphere of the room to be tested. Moreover, the described construction of the division 84 is such as to prevent the settling out of particles by providing a smooth flow without protected areas or creation of eddy currents. A second tier of divisions 88 and 90 includes like constructions.

The illustrated manifold has a three tier structure. The first tier is the inlet passageway 66, while the second tier is comprised of the two reduced passageways 68 and 70 and the third tier includes the four outlet passageways 72–78. A cross sectional area of tier flow passage through each tier is substantially identical. That is, the sum of the cross sectional areas of the two reduced passageways 68 and 70 generally corresponds to the cross sectional area of the inlet passageway 66, as well as the total of the four cross sectional areas of the four outlet passageways 72–78. In this manner the construction of the manifold 12 guards against changes in temperature, pressure and velocity which would result from a significant change in cross sectional area. An increase or decrease in pressure could result in the evaporation or condensation of vapors to jeopardize the particle count. Any decrease in velocity could result in larger particles settling out. Therefore construction of the manifold is an important factor in obtaining an accurate qualitative and quantitative analysis of a gas stream.

Referring to the drawings in general, in operation each of the sensors 14-20 includes a laser diode which directs an incident beam in the direction of a mirror mount 92 attached to the sensor. An aggregate sample flow enters the manifold 12 through an aerosol inlet conduit 22, as shown by arrow A. This aggregate sample flow is typically at a standardized flow rate, e.g., one cubic foot per minute. The aggregate sample flow is divided into four partial sample flows by the inlet manifold 12. These partial sample flows are represented by arrows from the nozzles 40 and 42 shown in FIG. 2. The intersections of the partial sample flows with the incident beam 50 and 52 define independent view volumes. Particles that enter the view volumes scatter light which is reflected, collected and sensed to provide electrical signals characterized by the sensed energy. The four readings are then combined. A large particle scatters a greater amount of light than does a small particle. Consequently, the pulse which is produced by a large particle traveling through a view volume has a greater amplitude. Conversely, a small particle is capable of causing only a small amplitude pulse, and therefore the presence of a relatively small particle is more likely to go undetected. By dividing the aggregate sample flow into a plurality of partial flows, the velocity through the view volume in which a particular particle is to be detected will be reduced. Since a particle causes a scattering of light during the entire time that the particle is illuminated by the incident beam, the decrease in velocity causes an increase in the total quantity of scattered light. This has two effects. Firstly, the increase of total scattered light enhances the possibility of relatively small particles being detected. Thus, the lower limit of particle detection is reduced. Secondly, because particles are present within the view volume for a greater time span, the minimum expected pulse width is increased. A flow rate which is decreased by a factor of four results in any particle spending four times as much time within a view volume. This quadruples the length of the detection pulse. The increase in the minimum pulse width allows amplifiers to have a reduced noise bandwidth, thereby improving the signal-to-noise ratio.

Although the present invention has been illustrated as having four sensors 14-20, this is not critical. In fact, in many applications a total of ten sensors would be optimum. Ten sensors allow an aggregate sample flow of 1 cfm to be divided into substantially identical partial sample flows of 0.1 cfm, whereas the illustrated embodiment of four sensors would limit the aggregate flow rate to 0.4 cfm if the partial flows are to be 0.1 cfm. Moreover, it is not critical that the partial sample flows remain parallel to each other. The partial sample flows may be at an angle relative to each other. Likewise, the detectors may be oriented to be at an angle relative to the incident beam. It has been discovered that an angle of approximately 70 degrees is optimum.

I claim:

1. An apparatus for detecting and counting particles in a gas stream flowing at a preselected rate comprising,
    channeling means for receiving a sample gas stream flowing at said preselected rate and for dividing said sample gas stream into a plurality of partial streams, and
    a plurality of substantially identical sensors, each sensor having a flow path in fluid communication with said channeling means to receive an associated one of said partial streams, each sensor having a light source means for projecting an incident beam in a direction to intersect said flow path and further having detection means for sensing light scattered by incidentbeam impingement of particles suspended in said associated partial stream.

2. The apparatus of claim 1 wherein said light source means of each sensor is a laser diode.

3. The apparatus of claim 1 wherein said channeling means is a manifold having an inlet and a plurality of outlets, the number of said outlets corresponding to the number of said sensors.

4. The apparatus of claim 3 wherein said manifold has a dividing structure of passageways from said upstream inlet to said downstream outlets, each division being a division of a single upstream passageway into a pair of downstream passageways.

5. The apparatus of claim 4 wherein said dividing structure of said manifold defines a plurality of tiers, said passageways increasing by a factor of two from an upstream tier to a downstream tier, for each tier the sum of the cross sectional areas of the passageways being generally equal to the sum of the cross sectional passageway areas of each other tier.

6. The apparatus of claim 5 wherein each division of passageways is defined by smooth radius turns.

7. The apparatus of claim 1 wherein said preselected rate of gas flow is 1 cfm.

8. An apparatus for monitoring particle content in a gas flow of a preselected rate comprising,
    a plurality of substantially identical sensing means, each having a fluid flow path and a laser source directed to project an incident beam through said fluid flow path to define a view volume, each sensing means further having a detector disposed to monitor scattered light from said view volume, and
    means for directing a plurality of substantially identical gas streams through said fluid flow paths, said gas streams having an aggregate flow rate equaling a preselected flow rate for monitoring particle content.

9. The apparatus of claim 8 wherein said means for directing said gas streams is a manifold having a plurality of tiers of passageways, said manifold having an inlet and a plurality of outlets, said passageways of each tier having a total cross sectional area equal to the passageway cross sectional areas of adjacent tiers.

10. The apparatus of claim 8 wherein said laser sources are laser diodes.

11. The apparatus of claim 8 wherein said detectors are photodetectors.

12. The apparatus of claim 9 wherein said manifold is attached to inlets of said fluid flow paths of said plurality of sensor means.

13. An apparatus for monitoring particles in a gas comprising,
    conduit means for supplying a gas flow at a set rate,
    manifold means in communication with said conduit means for splitting said gas flow into a plurality of partial gas flows and for channeling said partial gas flows to outlets, said partial gas flows having substantially identical rates, a plurality of sensor bodies, each having a fluid pathway in communication with one of said partial gas flows, a plurality of light sources, each disposed with respect to an associated sensor body to project an incident beam along an optical axis intersecting said fluid pathway of said associated sensor body to define a view volume, and a plurality of detector means for monitoring variations in light scattering in said view volumes.

14. The apparatus of claim 13 wherein each detector means is optically coupled to a single sensor body to monitor the sample region of that sensor body.

15. The apparatus of claim 13 wherein said light sources are laser diodes.

16. The apparatus of claim 13 wherein said conduit means supplies a gas flow at a rate of 1 cfm.

17. The apparatus of claim 13 wherein said manifold means is a manifold member having a plurality of passageway bifurcations from an inlet to said outlets, said bifurcations being defined by manifold walls having smooth radius turns and each bifurcation having a single upstream passageway and a pair of downstream passageways that have a combined cross sectional area generally equal to the cross sectional area of said upstream passageway.

18. The apparatus of claim 17 wherein said manifold member has a plurality of tiers, said tiers increasing the number of passageways by a factor of two from said inlet to said outlet.

19. The apparatus of claim 17 wherein said bifurcations define generally ninety degree turns.

20. The apparatus of claim 13 wherein said plurality of detector means each include a photodetector.

* * * * *